United States Patent
Mennen

(10) Patent No.: US 10,633,331 B2
(45) Date of Patent: Apr. 28, 2020

(54) METHOD OF MAKING A UREA PRODUCT

(71) Applicant: Stamicarbon B.V., Sittard (NL)

(72) Inventor: Johannes Henricus Mennen, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 15/326,434

(22) PCT Filed: Jul. 16, 2015

(86) PCT No.: PCT/NL2015/050523
§ 371 (c)(1),
(2) Date: Jan. 13, 2017

(87) PCT Pub. No.: WO2016/010432
PCT Pub. Date: Jan. 21, 2016

(65) Prior Publication Data
US 2017/0204054 A1 Jul. 20, 2017

(30) Foreign Application Priority Data
Jul. 17, 2014 (EP) .................................. 14177541

(51) Int. Cl.
*C07C 273/16* (2006.01)
*B01D 9/00* (2006.01)
*B01D 21/26* (2006.01)

(52) U.S. Cl.
CPC .......... *C07C 273/16* (2013.01); *B01D 9/0022* (2013.01); *B01D 21/262* (2013.01)

(58) Field of Classification Search
USPC ....................................................... 564/73
See application file for complete search history.

(56) References Cited

U.S. PATENT DOCUMENTS 3,123,637 A * 3/1964 Lard et al. .............. C05C 9/005
432/11
3,378,584 A * 4/1968 Hollowell ............... C05C 9/005
257/586

FOREIGN PATENT DOCUMENTS

EP 2 153 880 2/2010
WO WO-2013/055219 4/2013

OTHER PUBLICATIONS

AGP-Fertilizer Specification Aug. 1, 2009, p. 1-2.*
International Search Report for PCT/NL2015/050523, dated Oct. 2, 2015, 3 pages.
Meessen, "Urea" in: Ullmann's Encyclopedia of Industrial Chemistry, Wiley-VCH Verlag GmbH & Co. KGaA, Weinheim, Germany (2010) p. 33.

* cited by examiner

*Primary Examiner* — Ana Z Muresan
(74) *Attorney, Agent, or Firm* — Morrison & Foerster LLP

(57) ABSTRACT

Disclosed is a process for the preparation of a urea product suitable for being diluted with water so as to form an aqueous urea comprising solution for use in a unit for the reduction of NOx in combustion engine exhaust gases, also known as Diesel Exhaust Fluid (DEF) or to be used in De NOx systems of exhaust vapor from industrial furnaces. The process comprises obtaining an aqueous urea solution from or after a recovery section in a urea production process. This solution, which has a low content of impurities, is subjected to flash crystallization at a low pressure, so as to obtain a solid crystallized urea containing product, which is a free-flowing powder containing less than 0.2 wt. % water. This product is packaged under conditions such that the water content in the packaged product is maintained below 0.2 wt. %. The invention can also be used in a method of increasing the capacity of an existing urea plant.

12 Claims, 1 Drawing Sheet

METHOD OF MAKING A UREA PRODUCT

CROSS-REFERENCE TO RELATED APPLICATIONS

Figure 1:
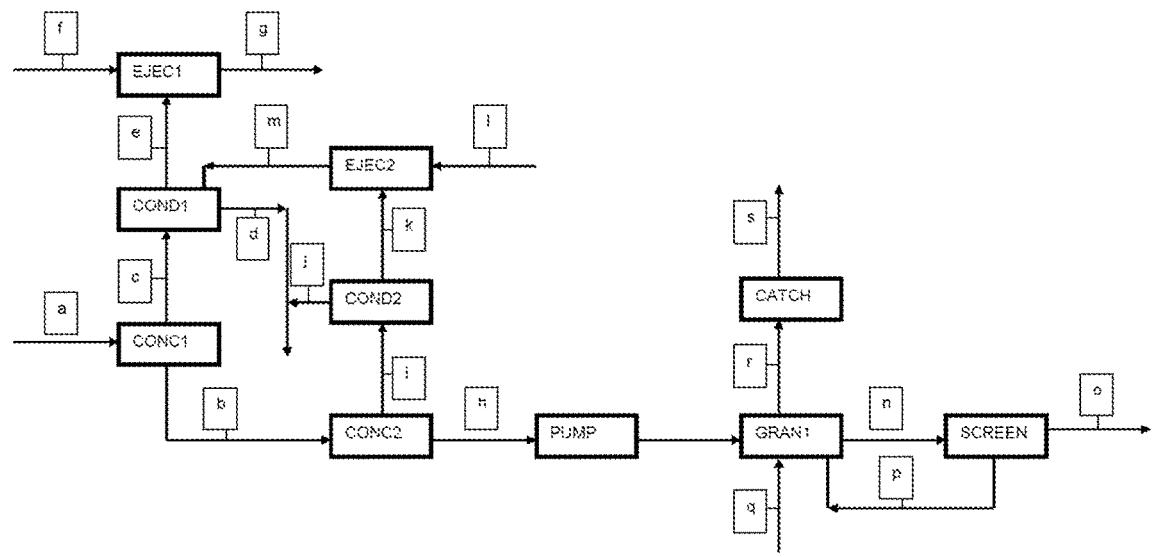

This application is the national phase of PCT application PCT/NL2015/050523 having an international filing date of 16 Jul. 2015, which claims benefit of European patent application No. 14177541.1 filed 17 Jul. 2014. The contents of the above patent applications are incorporated by reference herein in their entirety.

FIELD OF THE INVENTION

The invention is in the field of the production of solid urea, and particularly pertains to the production of a urea powder suitable for the preparation of a solution for NOx abatement such as used in selective reduction, which may be a non-catalytic thermal process or a selective catalytic reduction (SCR) process. An example of a solution for SCR is diesel exhaust fluid (DEF). The invention also pertains to a related method for increasing the capacity of an existing urea plant.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis section. Typical urea production plants further comprise a recovery section and a finishing section. In the recovery section non-converted ammonia and carbon dioxide are recovered and recirculated to the synthesis section. In the finishing section, typically, a urea melt is brought into a desired solid, particulate form, generally involving techniques such as prilling, granulation, or pelletizing.

The present invention relates to the production of solid urea, i.e. to urea finishing, A background reference relating to urea finishing is WO 2013/055219. Therein a method is disclosed wherein urea crystals are produced by subjecting a urea solution to flash crystallization, and subsequently a shaping step wherein the urea crystals are subjected to mechanical force.

An end-use of urea that is of increasing practical importance, is in the form of an aqueous solution for the abatement of nitrous oxides formed in combustion processes. The solution is known as diesel exhaust fluid (DEF), available, e.g., under the trademark AdBlue®, and is typically used in vehicles with diesel engines to reduce NOx formed during the combustion of diesel fuel. The reduction typically takes place with the help of a catalyst at elevated temperatures. During the reaction, the urea decomposes in ammonia and $CO_2$, whereby the ammonia reacts in turn with the nitrous oxides in the exhaust gas stream of the diesel engine to form nitrogen and water.

A urea solution for use as DEF needs to meet stringent requirements, in particular with respect of the level of by-products, such as biuret (max 0.3%) and ammonia, and additives used during the urea finishing process, such as formaldehyde. The by-products and additives are allowed only in minor amounts in the DEF solution. These requirements are laid down in international standards such as DIN V70070 and ISO 22241. These standards are identical with respect to the specification.

Several methods have been described to produce DEF solution, e.g. by diluting urea granulate or prills in water. Typical problems associated with diluting urea after finishing, is the relatively high level of biuret and the presence of additives, such as formaldehyde which is added to increase the strength of the particles and reduce caking (stickiness). With reference to the aforementioned standards, the additives typically need to be removed to make the solution suitable for use as DEF, which requires costly and energy intensive processes.

A background reference relating to a method that avoids the need for removing additives, is disclosed in EP1 856 038. Therein, a DEF solution is prepared by taking a urea comprising aqueous stream separated directly from or after a recovery section in a urea production process, and thereafter diluting with water until the urea comprising stream comprises 30-35 wt. % urea. This method advantageously provides a solution which is directly suitable as DEF. However, since the end-product is a solution, its distribution in effect means that about two thirds water are transported, which is costly and which requires tank wagons instead of standard lorries.

Producing and handling a solution cannot be easily avoided. Urea is a product which is known to have properties which are not favorable for bulk transportation. In powder form urea is very sticky and is not free flowing. As the most common application of urea is that as fertilizer which is distributed over agricultural land, it is necessary to provide the final urea product in the form of a solution in water or as free flowing pellets which can be easily distributed. Two main processes are in use to produce these pellets. Firstly prilling, which involves contacting droplets of melted urea with a stream of cooling air in a prilling tower. The cooling air removes the heat of crystallization and the prills are collected at the bottom of the prilling tower. A disadvantage of prills is that the size of the pellets as well as the mechanical strength is limited and the prills tend to stick together during transportation over significant distances. This effect is called caking. A second process is fluid bed granulation which is successful in addressing some of these problems. The granules are typically larger than the prills and show a lower tendency to caking which makes them more suitable for transportation. Typically, additives such as formaldehyde are added to the urea melt before granulation to further improve the strength of the granulate and reduce the caking tendency. These additives, as referred to above, are undesirable, if not straightforwardly prohibitive, for using the resulting urea in DEF.

It is therefore desired to provide a urea product, suitable for the production of DEF, which has a sufficient purity of its own to meet the specifications for DEF, but which does not require transporting a great amount of water as of its production site. Particularly, it is desirable to have a free flowing urea powder for the preparation of a DEF solution.

In the art, no free flowing urea powder that can be transported to the desired location and subsequently be used to easily prepare a DEF solution, is as yet unknown.

It would further be desired to provide a urea powder that can be used to prepare a solution for treating flue gases from industrial furnaces such as reformers. Herein a thermal rather than a catalytic process can be used, and the applied solutions are generally more concentrated than DEF. It is generally difficult to transport a concentrated urea solution, due to the possible precipitation of solid urea at lower temperatures. Whilst a more diluted solution could be transported, such would bring about additional costs and efforts to transport water, and it would require additional energy input to increase the concentration before use. Therefore having a suitable urea powder as a starting material, would provide additional flexibility and cost saving in transportation.

SUMMARY OF THE INVENTION

In order to better address one or more of the foregoing desires, the invention, in one aspect, provides a process for the production of a urea product suitable for being diluted with water so as to form an aqueous urea comprising solution for use in a unit for the reduction of NOx that can be used in combustion engine exhaust gases, the process comprising:

(a) obtaining an aqueous urea stream from or after a recovery section in a urea production process;

(b) subjecting said solution to flash crystallization at a subatmospheric pressure, so as to obtain a solid crystallized urea containing product and an ammonia and water containing vapor, wherein the solid crystallized urea product contains less than 0.2 wt. % water;

(c) packaging the solid crystallized urea product under conditions such that the water content in the packaged product is maintained below 0.2 wt. %.

In another aspect, the invention presents a method of making an aqueous solution comprising 30-70 wt. % urea, by dissolving a solid crystallized urea product obtainable by the aforementioned method.

In a further aspect, the invention presents a method of modifying an existing urea plant comprising a finishing section for the production of solid urea, the method comprising adding to the plant a device suitable for the flash crystallization of urea from a solution, preferably a device suitable for dry flashing.

In a still further aspect, the invention is a method for increasing the plant capacity of a urea plant comprising increasing the capacity of a finishing section of said plant by adding, as an additional finishing section, a device suitable for crystallizing urea from a solution by flashing, preferably by dry flashing.

DETAILED DESCRIPTION OF THE INVENTION

In a broad sense, the invention is based on the judicious insight that a flash crystallization of urea, and providing a water content below a certain level, as defined above, produces surprisingly a free flowing powder. I.e, it will be understood that the aforementioned solid crystallized urea containing product is a powder. This powder is not prone to agglomeration and lump formation. This powder can be easily transported, easily packaged and subsequently easily removed from its package, and can be dissolved in order to produce i.e. diesel exhaust fluid. Particularly, a diesel exhaust fluid of excellent quality can thereby be obtained.

Another aspect of the produced solid urea according the invention is the low biuret content. Biuret is a polymerization product of urea that is formed at increased urea concentrations at increased temperatures and retentions. Biuret is a negative component in the urea used for DeNOx systems since exposure of the biuret component to the catalyst causes isocyanuric acid formation that decreases the life time of the catalyst. Therefore a lower biuret content in the supplied urea solid to be used for i.e. DEF solution extends the lifetime of said DeNOx catalyst.

Hereinafter the urea powder obtained in accordance with the invention is sometimes referred to as "DEF powder".

This does not imply that its use is limited to DEF. In fact, the powder is not only highly suitable for preparing a DEF solution, but also for making more concentrated solutions, typically for industrial use, e.g., for treating flue gases to eliminate NOx components into nitrogen and water from industrial furnaces such as reformers.

In accordance with the invention, the urea product obtained is to be diluted with water so as to form an aqueous urea comprising solution. Particularly, the urea product is suitable for being diluted with water so as to form an aqueous urea comprising solution that meets the requirements for DEF. These requirements have been standardized as ISO 22241-1:2006 (version of 15 Oct. 2006).

In the process of the invention, an aqueous urea solution is used that is obtained from or after a recovery section in a urea production process. This can generally be done by separating a urea-comprising aqueous stream from an existing urea production process. The urea-comprising aqueous stream can be the total urea-comprising stream resulting from the urea process or it can be a part of it.

It is also possible to design a new urea process that is particularly suitable for the production of a urea-comprising aqueous stream that will be used in a unit for the reduction of NOx in combustion engine exhaust gases. An advantage of the design of a new urea process is that this new process does not need to comprise a shaping section.

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis zone. The resulting urea formation can be presented best in the form of two consecutive reaction steps, in the first step ammonium carbamate being formed according to the exothermic reaction:

after which the ammonium carbamate formed is dehydrated in the second step to give urea according to the endothermic equilibrium reaction:

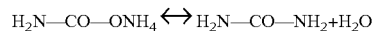

The extent to which these reactions take place depends among other things on the temperature and the ammonia excess used. The reaction product obtained in a urea synthesis solution substantially consists of urea, water, unbound ammonia and ammonium carbamate. The ammonium carbamate and the ammonia are removed from the solution and are generally returned to the urea synthesis zone. In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

In a urea stripping plant the decomposition of the ammonium carbamate that has not been converted into urea and the expulsion of the usual ammonia excess largely takes place at a pressure that is essentially almost equal to the pressure in the synthesis reactor. This decomposition and expulsion take place in one or more stripper(s) installed downstream of the reactor, possibly with the aid of a stripping gas such as, for example, carbon dioxide and/or ammonia, and with the addition of heat. It is also possible to apply thermal stripping. Thermal stripping means that use is made exclusively of the supply of heat to decompose ammonium carbamate and remove the ammonia and carbon dioxide present from the urea solution. The gas stream leaving a stripper contains ammonia and carbon dioxide which are condensed in a high-pressure condenser and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa. The ammonia to carbon dioxide molar ratio (N/C ratio) in the urea synthesis zone of a stripping plant lies usually in between 2.2 and 5 and preferably between 2.5 and 4.5 mol/mol. The synthesis zone can be carried out in a single reactor or in a plurality of reactors arranged in parallel or series. After the stripping treatment, the pressure of the stripped urea solution is reduced in a urea recovery section.

In a recovery section of a urea production plant, including but not limited to stripping plants, the non-converted ammonia and carbon dioxide in the urea solution is separated from the urea and water solution. A recovery section usually comprises a heater, a liquid/gas separation section and a condenser. The urea solution entering a recovery section is heated to vaporize the volatile components ammonia and carbon dioxide from that solution. The heating agent used in the heater is usually steam. The formed vapor in said heater is separated from the aqueous urea solution in the liquid/gas after which said vapor is condensed in the condenser to form a carbamate solution. The released condensation heat is usually dissipated in cooling water. The formed carbamate solution in that recovery section operated at a lower pressure than the pressure in the synthesis section is preferably returned to the urea synthesis section operating at synthesis pressure. The recovery section is generally a single section or can be a plurality of recovery sections arranged in series.

The urea-comprising aqueous stream is separated directly from or after a recovery section in the urea production process. The urea-comprising aqueous stream may come from one recovery section but also, if the urea production process comprises more recovery sections, from several recovery sections. The urea-comprising aqueous stream can be one stream that is separated from one location in the urea production process or it can be composed of several streams that are separated at various locations from the urea production process.

In the recovery section(s) of a urea production process the ammonium carbamate, free carbon dioxide and free ammonia content of the urea synthesis solution is reduced. This is done by heating the solution and optionally by reducing the pressure. This temperature increase and optionally also pressure decrease causes the ammonium carbamate that is present to dissociate into free ammonia and free carbon dioxide. A substantial part of this free ammonia and free carbon dioxide passes into the gas phase, which is separated from the rest of the urea-comprising aqueous stream in liquid/gas separators. In the various urea production processes different pressure and temperature levels are applied in the recovery section(s). In some processes a stripping medium is added to one or more dissociation steps in order to promote the dissociation process. Examples of a suitable stripping medium are ammonia gas, carbon dioxide gas, air and steam. The various processes also differ in the way in which the expelled gaseous ammonia and carbon dioxide are processed. While the urea solution flows through the various dissociation steps, the alkalinity and the ammonium carbamate content are reduced.

Preferably, the urea-comprising aqueous stream is separated after the recovery section(s). Generally, said stream will be separated before a urea finishing section, although it could also be separated after a first evaporator downstream of a recovery section, which evaporator may or may not be considered to be part of a finishing section. At any rate, the urea-comprising aqueous stream will generally have a urea concentration of below 99 wt. %.

In a urea process, wherein a urea storage tank is present after the recovery section(s) and, when a shaping section (such as for granulation or prilling) is present, before the shaping section, the aqueous urea solution is, more preferably, a urea-comprising aqueous stream separated from the urea storage tank. The urea-comprising aqueous stream that is separated directly from or after a recovery section in a urea production process preferably comprises 60-90 wt. % urea.

In the process of the invention, the urea-comprising aqueous stream obtained as described above, is subjected to flash crystallization. Therein the solution is subjected to flashing so as to obtain a solid crystallized urea containing product and an ammonia and water containing vapor. The flashing preferably is dry-flashing. The flash crystallization is conducted by subjecting a urea solution to sub-atmospheric conditions so as to allow the spontaneous formation of urea crystals. Preferably, prior to the crystallization step, the solution is concentrated so as to have to a urea concentration of 50% to 99% by weight of urea and biuret, and preferably of from 60% to 98% by weight.

As noted above, the solid crystallized urea product is obtained in the form of a powder containing less than 0.2 wt. % water. This can be the direct result of the flashing process, particularly in the event of dry flashing. Alternatively, in an interesting embodiment, the flashing results in a powder having a water content higher than 0.2 wt. % (but low enough so as to have a powder, e.g, between 0.2 and 0.5 wt. %). In such event, the solid crystallized urea product that contains less than 0.2 wt. % water, is obtained by subjecting said powder to a drying step, e.g. in a drying column, or by subjecting it to evaporation on a heated moving belt.

To better address possible stickiness, the optimum inlet urea concentration subjected to flashing is in a range of from 85 wt. % and 95 wt. %, preferably between 86 wt. % and 93 wt. %, and more preferably between 87 wt. % and 92 wt. %. At these concentration ranges, and taking into account the pressures applied, solids (urea) and gas ($H_2O$) are in equilibrium.

The solid crystallized urea product of the invention can be obtained on the basis of any urea synthesis process.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section is followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution. The invention is not limited to any particular urea production process. Other processes and plants include those that are based on $CO_2$ technology such as total recycle plants, the HEC process developed by Urea Casale, the ACES process developed by Toyo Engineering Corporation and the process developed by Snamprogetti. All of these processes, and others, may be used preceding the urea finishing method of the invention.

In the invention, a urea solution obtained in any urea synthesis process, is subjected to a crystallization step by subjecting the urea solution to expansion by being brought under conditions of sub-atmospheric pressure, i.e., by flashing. This type of crystallization is very suitable with a view to commercial scale processing. The crystallization step comprises flashing the urea solution at subatmospheric pressure, preferably at a pressure below 15 kPa so as to spontaneously obtain a solid urea product. Said pressure will generally be above 1 kPa, and preferably in a range of from 1 to 10 kPa.

In one embodiment hereof, the urea solution formed in a recovery section from a urea plant is sent to a crystallizer operated at a pressure in the aforementioned ranges. Urea crystals are formed spontaneously by expansion, with formation of vapor. The formed vapor is subjected to condensation in one or more condensers. The urea crystals including the remaining urea solution leaving the crystallizer is subjected to separation in a liquid to solid separator, where the bulk of urea solution is separated from the formed urea crystals. Said urea crystals leaving the liquid to solid separator are subjected to a centrifuge in which the left urea solution is further separated from said crystals. A mother liquor comprising an aqueous urea solution that comprises biuret can be added to the centrifuge in order to wash said crystals in order to obtain purified urea crystals comprising a biuret content in between 0.1 and 0.6% by weight only. DEF solutions produced therefrom, having a concentration of 30-35 wt. % urea, will thus satisfy the requirement of having maximally 0.3 wt. % of biuret.

The urea crystals leaving the centrifuge are further dried, e.g., in a drying column, so as to provide a solid crystallized urea product containing less than 0.2 wt. % water.

The released vapor after the expansion of the urea solution is increased in pressure and transported to a condenser. Preferably a steam ejector or a vacuum pump is used for increasing the pressure. In the condenser the vapor comprising water and small amounts of impurity components like ammonia and carbon dioxide and inert, is condensed. Preferably cooling water is used for condensing said vapors. The non condensed vapors leaving the condenser are subjected to a steam ejector or a vacuum pump to increase pressure where after a further purification of these vapors take place. This can be done by again condensing these vapors at a higher pressure where after the left inert vapor is released into the atmosphere or is again purified in an inert purification unit as for example an absorber. The formed process condensate in the condensers is collected where after said process condensate is subjected to a process condensate purification in the urea plant.

Flashing the urea solution, i.e. removing liquid by evaporation under reduced (subatmospheric) pressure, results in the spontaneous formation of a solid urea product and an ammonia and water containing vapor. In accordance with the invention, the flashing is preferably conducted at a pressure of below 15 kPa, more preferably of from 1 kPa to 10 kPa.

Flashing can be done in a flashing device, such as a dry flasher. A dry flasher is characterized in that a liquid stream is converted by crystallization and evaporation into substantially a solid and a vapor. In a dry flasher the process conditions are selected such that the amount of liquid remaining is substantially nil. This allows for a clean separation of the gas and the solids without substantial sticking and fouling. Another advantage of the dry flashing is that due to the absence of a slurry, no solid liquid separation such as a centrifuge, nor a re-melter is necessary. This allows a significantly simpler process scheme. Such a dry flasher is a vessel that operates preferably at a pressure in between 1 and 15 kPa and more preferably at a pressure in between 2 and 10 kPa. In said dry flasher the urea solution is distributed by a liquid distributer. By the expansion the urea and biuret crystallizes spontaneously in a solid and the remaining components comprising water, ammonia and small amounts of carbon dioxide evaporate.

The particle size of the obtained solid urea product by adiabatic flashing, i.e., the urea powder, is in the range of from 0.1 µm to 1000 µm, preferably of from 1 µm to 800 µm.

The process of the invention allows to produce a free flowing powder which can be packaged in bags (20 kg) or big bags (i.e., 500 kg or 1000 kg bags) which can be easily emptied on site to produce the DEF solution.

The urea powder produced by the process has a very low quantity of biuret, typically less than 0.5%, preferably less than 0.4% which translates into less than 0.20% or less than 0.15% wt. in the final DEF solution. This means that the amount of active urea in the solution will be consequently higher at the same solids content. The biuret specification for the final DEF solution is max 0.3% wt. When prills are used to prepare the solution, the biuret content in the solution is typically between 0.25 and 0.3% wt.

In the method of the invention, the solid crystallized urea product as obtained, is packaged under conditions such that the water content in the packaged product is maintained below 0.2 wt. %. This low moisture content serves to ensure that the solid urea, which is hygroscopic by nature, remains a powder that is capable of being released from its package, and reconstituted to a solution. According to the invention, the water content in the packaged product is maintained below the aforementioned level until the product is to be used for preparing a solution. It will be understood that the process of the invention implies, after obtaining the crystallized urea powder that contains less than 0.2 wt. % water, maintaining said water content below 0.2% not only in the packaged product, but also during further process steps prior to the packaging.

In practice this means that the powder obtained, which has the required low moisture content, is packaged in a non water-permeable package (e.g. a container or a bag). Suitable packaging materials include high density polyethylene. Other plastics suitable for packaging hygroscopic materials are known in the art. The packing material may be non-porous and sealed. Also, the package can consist of multi-layer material.

In an interesting embodiment, the invention can also be put to use in modifying existing urea plants. Such existing urea plants, which will normally have a finishing section based on prilling or granulation, can be modified by adding equipment suitable for conducting the flash crystallization step according the above described method. By thus adding to the conventional finishing section, a flash crystallization section, the plant will be capable of producing both a conventional solid urea form, viz. granules or prills, and a DEF powder as described hereinbefore.

Particularly, the invention can thereby be used in order to increase the capacity of an existing urea plant. The finishing section can sometimes be a bottleneck in optimizing the capacity of a plant. Since traditional finishing sections, particularly in the cases of prilling towers, are relatively large, it is not always possible to expand the finishing section of an existing plant. By virtue of the present invention, it is possible to increase the capacity of an existing urea plant by increasing the capacity of a finishing section of such a plant. This refers to any situation in which the finishing section of the existing plant would need to be expanded in order to increase the capacity of the plant. This can refer to a plant having a synthesis and recovery capacity that is not used to its full capacity, due to the finishing section being a bottleneck. It can also refer to a method of increasing the capacity of an existing urea plant wherein the capacity of the urea synthesis section (and/or of the urea recovery section) is increased, e.g. by expanding the synthesis section, but wherein the existing finishing section cannot be easily expanded. The present invention then allows to accommodate the expansion of the section, or sections, upstream of the finishing section, by an advantageously simple method to expand also the capacity of the finishing section. This can be carried through adding, parallel to the existing finishing section, a finishing section according to the invention, i.e., a device suitable for crystallizing urea from a urea solution. In accordance with the invention, the problems associated with increasing the capacity of the finishing section are addressed, since the parallel alternative finishing section will go with reduced, or even avoided, emissions of gaseous ammonia and urea dust. Thus, with the capacity of the plant increased, the emissions per quantity of produced urea are in fact reduced.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein more than one aqueous stream is separated from different places in or after the recovery section, to obtain the aqueous urea solution to be subjected to flash crystallization.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage.

In sum, the invention includes a process for the preparation of a urea product suitable for being diluted with water so as to form an aqueous urea comprising solution for use in a unit for the reduction of NOx in combustion engine exhaust gases, also known as Diesel Exhaust Fluid (DEF) and in a unit for the reduction of NOx in flue gases from industrial furnaces. The process comprises obtaining an aqueous urea solution from or after a recovery section in a urea production process. This solution, which has a low content of impurities, is subjected to flash crystallization at a low pressure, so as to obtain a solid crystallized urea containing product, which is a free-flowing powder containing less than 0.2 wt. % water. This product is packaged under conditions such that the water content in the packaged product is maintained below 0.2 wt. %. The invention can also be used in a method of increasing the capacity of an existing urea plant.

The invention will hereinafter be further illustrated with references to the following, non/limited examples. The state of the art is illustrated in FIG. 1 while the embodiments of the invention are shown in FIG. 2

Figure 2:
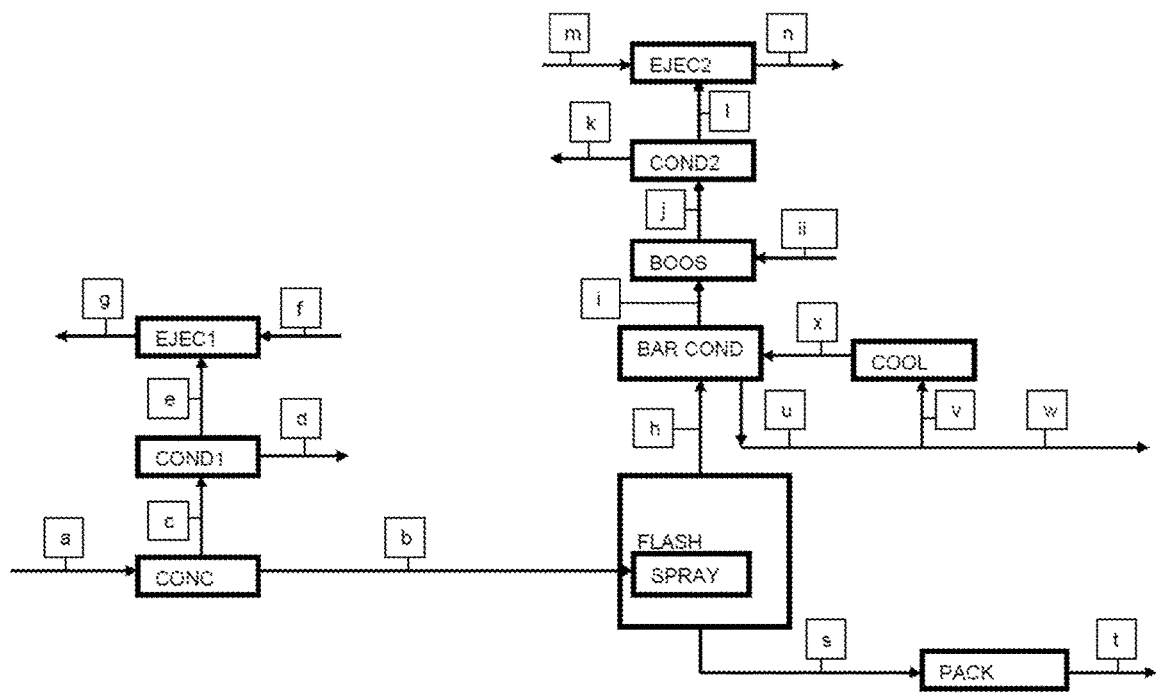

FIG. 1 shows a typical sequence for concentrating a urea solution to a urea melt where after the urea melt is subjected to a typical granulation unit as urea finishing section as known from the prior art. Urea solution from a recirculation section of a urea plant with a typical concentration in between 50 and 80% by weight and a typical temperature in between 60 and 90° C. is added to a concentrator (CONC1) via line (a). The concentrator (CONC1) is a shell and tube heat exchanger and the urea solution is subjected to the tube side of said concentrator. At the shell side of said concentrator steam is added to heat the solution and to evaporate the volatile water fraction. The urea solution leaving the concentrator (CONC1) via line (b) has typically a temperature of 125 to 135° C. and is concentrated to typically 93 to 96% by weight of urea. The pressure in said concentrator is sub-atmospheric and typically in between 20 to 50 kPa. The formed vapor comprising water and small amounts of ammonia and carbon dioxide is discharging said concentrator via line (c). Said vapor is condensed in a condenser (COND1) and leaves said condenser as process condensate via line (d). Non-condensed vapor is leaving said condenser via line (e) and is subjected to an ejector (EJEC1) to increase the pressure to atmospheric pressure. The driving force for said ejector is usually steam via line (f). The steam together with the non-condensed vapor leaves said ejector via line (g) and can be subjected to the atmosphere but preferably is purified in the urea plant itself.

The urea solution leaving the concentrator (CONC1) via line (b) is subjected to a second concentrator (CONC2). Also this concentrator (CONC2) is typically a shell and tube heat exchanger where the urea solution is subjected to the tube side of said heat exchanger while steam is added to the shell side to heat and vaporize the volatile water fraction at sub atmospheric pressure that is typically in between 1 to 30 kPa and preferable in between 5 and 20 kPa. The temperature of the urea melt leaving said concentrator via line (h) is typically in between 136 and 145° C. and comprises typically a concentration in between 97.5 to 99% by weight of urea and biuret. The formed vapor formed by the concentration of said solution to said melt comprising water, ammonia and some entrained urea, is subjected to a condenser (COND2) via line (i). In said condenser (COND2) the bulk of vapor is condensed to form process condensate by the aid of cooling water. The formed process condensate leaves said condenser via line (j). The non-condensed vapor leaving said condenser (COND2) comprising inert, water and small amounts of ammonia via line (k) is subjected to a steam ejector (EJEC2). Said ejector is driven by steam via line (l) and increases the pressure of said inert vapor that leaves said ejector via line (m) to the condenser (COND1).

The urea solution leaving said concentrator (CONC2) via line (h) is sent by a pump (PUMP) to a fluid bed granulator (GRAN1) as urea finishing section. An additive such as formaldehyde or urea formaldehyde solution can be added to said urea solution. Ordinary fluid-bed granulation processes comprises a granulator (GRAN1) in which urea melt is fed to a fluid bed of solid urea nuclei upon the nuclei grow by solidification to obtain urea granules. The obtained granules have a certain size distribution when leaving said granulator. These granules are usually cooled where after these obtained granules are sent to a size classification unit via line (n) and in most cases this classification unit comprises a number of screens (SCREEN). By that classification unit the fines and the coarse material is separated from the remaining granules that is after a secondary cooling unit sent as product to a storage or transportation section via line (o).

The coarse material fraction is crushed to a certain granule size and recycled together with the fines fraction via line (p) into the granulator (GRAN1) where it acts as nuclei.

Air is supplied to the fluid bed granulator via line (q) to keep the solid nuclei in said granulator fluidized. The air discharging said granulator via line (r) comprises ammonia and urea dust and has to be treated in a urea dust catcher (CATCH) before the air is discharged into the atmosphere via line (s). Dependent of the amount of air supplied as air needed for fluidization in the fluid bed granulator (GRAN1) by line (q), the ammonia and dust emission in the air exhausted into the atmosphere via line (s) is typically in between 50 and 200 mg per normal m$^3$ respectively in between 20 and 50 mg per normal m3. This corresponds for the ammonia emission in between 0.5 and 1.5 kg per produced ton of urea end product and for the urea dust emission in between 0.2 and 1 kg per produced ton of urea end product.

FIG. 2 shows an example of the embodiment according to the invention.

Urea solution with a concentration of typically 50 to 80% by weight and a temperature of typically 60 to 90° C. is added to a concentrator (CONC) via line (a). The concentrator (CONC) is a shell and tube heat exchanger and the urea solution is subjected to the tube side of said concentrator. At the shell side of said concentrator steam is added to heat the solution and to evaporate the volatile water fraction. The urea solution leaving the concentrator (CONC) via line (b) has typically a temperature of 110 to 130° C. and is concentrated to 80 to 97% by weight of urea and preferably to a urea concentration of 85 and 95% by weight. The pressure in said concentrator is sub-atmospheric and typically in between 15 to 70 kPa and preferably in between 20 and 50 kPa. The formed vapor, comprising water and amounts of ammonia and carbon dioxide is discharging said concentrator via line (c). Said vapor is condensed in a condenser (COND1) and leaves said condenser as process condensate via line (d). Non-condensed vapor comprising inert, water, ammonia and carbon dioxide, leaves said condenser via line (e) and is subjected to an ejector (EJEC1) to increase the pressure to atmospheric pressure. The driving force for said ejector is usually steam via line (f). The steam together with the non-condensed vapor leaves said ejector via line (g) and can be subjected to the atmosphere but preferably is purified in the urea plant itself before releasing it into the atmosphere.

The urea solution leaving the concentrator (CONC) via line (b) is sent to a dry flasher (FLASH). Said dry flash is a vessel that operates at a pressure in between 1 and 20 kPa and preferably at a pressure in between 2 and 15 kPa. In said dry flasher the urea solution is distributed by a liquid distributer (SPRAY). By the expansion the urea and biuret crystallizes spontaneously in a solid and the remaining components comprising water, ammonia and small amounts of carbon dioxide evaporates.

The formed solid urea particles in the dry flasher (i.e. the aforementioned urea powder) have a particle size in between 0.1 and 1000 μm and are extracted from said dry flasher (FLASH) via line (s). Known extractors to extract solid product from vacuum systems are for example but not limited to air lock rotary feeders, seal vessel with double valves and venture ejectors. The extracted solid urea particles via line (s) are conveyed to a packaging (PACK) where said urea solid particles are bagged for transportation.

The formed vapor leaves the dry flasher (FLASH) via line (h) to a condenser (BAR COND). This can be a condenser of any type but preferably it is a direct contact condenser. In a direct contact condenser the vapor comes in direct contact with a cold medium. This medium can be a fluid comprising ammonia and water. It is expected that a portion of the formed small urea particles in the dry flasher (FLASH) will leave said dry flasher together with the formed vapor. Consequently these urea particles will dissolve in the medium and thus excessive fouling of the condenser (BAR COND) is prevented. The fluid leaving the condenser (BAR COND) via line (u) comprising water, small amounts of ammonia and dissolved urea is partly recycled via line (v) and cooled in a cooler (COOL). The other part of said fluid leaves the system via line (w). This fluid can be recycled and re-processed in the urea plant or can be used for other purposes.

The required sub-atmospheric pressure in the dry flasher (FLASH) and condenser (BAR COND) is maintained by a booster ejector (BOOS). The driving force for said booster ejector is steam supply via line (ii). The boosted vapor leaving said booster ejector via line (j) is subjected to a condenser (COND2). The formed process condensate leaves said condenser via line (k) while the non-condensed vapor leaving said condenser via line (l) is subjected to an ejector (EJEC2). Also said ejector is driven by steam via line (m) and increases the pressure of the vapor leaving said ejector via line (n) to atmospheric pressure and releases the inert vapor into the atmosphere or is preferably purified from ammonia elsewhere in the urea plant before releasing it into the atmosphere. The process condensate that leaves said condensers is collected and processed in the urea plant to become clean process condensate. In another embodiment the inert vapor leaving the ejector (BOOS) via line (j) is subjected to another condenser operated at a pressure below atmospheric where after the inert vapor leaving said condenser is increased in pressure to atmospheric by the application of a vacuum pump or steam ejector.

The invention claimed is:

1. A method for the production of a packaged product which is a free-flowing urea suitable for easily dissolving in water to obtain an aqueous urea comprising solution, the process comprising:
   (a) obtaining an aqueous urea stream from or after a recovery section in a urea production process;
   (b) subjecting said aqueous urea stream to flash crystallization at subatmospheric pressure, so as to obtain a free flowing crystallized urea powder and an ammonia and water containing vapor, wherein the crystallized urea powder contains less than 0.2 wt. % water;
   (c) directly packaging the crystallized urea powder as obtained in (b) into a non-water permeable package under conditions such that the water content in the packaged product is maintained below 0.2 wt. % to obtain said packaged product which is a free-flowing urea powder.

2. The method of claim 1, wherein the flash crystallization is conducted at a pressure below 15 kPa.

3. The method of claim 1, wherein the flash crystallization is conducted as dry flashing.

4. The method of claim 1, wherein the aqueous urea comprising solution is suitable for use in a unit for the reduction of NOx in combustion engine exhaust gases.

5. The method of claim 1, wherein the aqueous urea stream subjected to flash crystallization of (b) has a urea concentration in a range of from 85 wt. % to 95 wt. %.

6. The method of claim 1, wherein the biuret content of the crystallized urea powder obtained in (b) is at most 0.5 wt. %.

7. The method of claim 1, wherein the crystallized urea powder obtained in (b) has a particle size in the range of from 1 μm to 800 μm.

8. A method of making an aqueous solution comprising 30-70 wt. % urea, which method comprises dissolving the crystallized urea powder obtainable by the method of claim 1.

9. The method of claim 8 that results in an aqueous urea comprising solution comprising 30-35 wt. % urea suitable for use in a unit for the reduction of NOx in combustion engine exhaust gases.

10. The method of claim 8 that results in an aqueous urea comprising solution suitable for use in a unit for the reduction of NOx in exhaust vapors from industrial furnaces.

11. The method of claim 2, wherein the flash crystallization in (b) is conducted at a pressure from 1 to 10 kPa.

12. The method of claim 1, wherein the aqueous urea stream subjected to flash crystallization of (b) has a urea concentration in a range of between 87 wt. % and 92 wt. %.

* * * * *